United States Patent [19]

Merry

[11] Patent Number: 4,935,445

[45] Date of Patent: Jun. 19, 1990

[54] METHOD FOR TREATMENT TUMORS SENSITIVE TO TREATMENT WITH ANTI-TUMOR AGENTS EMPLOYING NORVERAPAMIL

[76] Inventor: Stephen Merry, 32 Southview Drive, Blanefield, Glasgow 963 9 JF, Great Britain

[21] Appl. No.: 174,366

[22] Filed: Mar. 28, 1988

[30] Foreign Application Priority Data

Mar. 31, 1987 [DE] Fed. Rep. of Germany ....... 3710806

[51] Int. Cl.$^5$ .................. A61K 31/275; A61K 31/70; A61K 31/44
[52] U.S. Cl. ..................................... 514/523; 514/33; 514/283; 424/10
[58] Field of Search ........................... 514/523, 33, 283

[56] References Cited

FOREIGN PATENT DOCUMENTS 0159678 10/1985 European Pat. Off. .

OTHER PUBLICATIONS

Benson, III, et al, Cancer Treatment Reports, vol. 69, No. 7–8, Jul./Aug. 1985, pp. 795–799.
Neugebauer, Cardiovascular Research, 1978, vol. 12, pp. 247–254.
McAllister et al, Clin. Pharmacol. Ther., Apr. 1982, pp. 418–426.
Chemical Abstracts 96: 210651w (1982).

Primary Examiner—Jerome D. Goldberg
Attorney, Agent, or Firm—Oblon, Spivak, McClelland, Maier & Neustadt

[57] ABSTRACT

Improvement in method for treating tumors sensitive to treatment with anti-tumor agents employing Norverapamil.

4 Claims, No Drawings

METHOD FOR TREATMENT TUMORS SENSITIVE TO TREATMENT WITH ANTI-TUMOR AGENTS EMPLOYING NORVERAPAMIL

German Patent 1,158,043 (cf. Example 3b) discloses α-isopropyl-α-(N-homoveratryl-γ-aminopropyl)-3,4-dimethoxyphenylacetonitrile (referred to below as norverapamil). It is described there as an intermediate for the preparation of verapamil.

Japanese Preliminary Published Application 83 624/1983 describes the use of verapamil for reinforcing the action of antitumor agents. However, A.B. Benson et al. (Cancer Treat. Rep. 69 (1985), 795) have found that the combination of verapamil and antitumor agents is restricted in its applications since the intrinsic cardiac action of verapamil excludes the use of a higher dose, which is necessary. The same applies to the treatment of tumor metastases (European Laid-Open Application 159,678) with verapamil alone.

Surprisingly, we have found that norverapamil can readily be used for assisting known tumor treatment since its cardio-vascular action is substantially weaker (Cardiovasc. Res. 12 (1978), 247) and it can therefore be administered in sufficiently high doses.

The present invention relates to norverapamil for use in the treatment of disorders.

Norverapamil can, if desired, be used in the form of its salts with physiologically tolerated acids. Preferred physiologically tolerated acids are hydrochloric acid, sulfuric acid, phosphoric acid, acetic acid, citric acid, malonic acid, salicylic acid, maleic acid, fumaric acid, succinic acid, ascorbic acid, malic acid, methanesulfonic acid, lactic acid, gluconic acid, glucuronic acid, amidosulfonic acid, benzoic acid and tartaric acid.

The dose of norverapamil as an antimetastasis agent assistant varies depending on the type of cancer and the stage of the disorder. As a rule, the daily dose for adults is from 300 to 1,000 mg for oral administration, from 200 to 300 mg for intravenous administration and from 200 to 500 mg for intraperitoneal administration.

Norverapamil can be in the form of tablets, capsules or coated tablets for oral administration and in the form of injection solutions for parenteral (i.v., i.p. or i.m.) administration. Solutions may also be infused. The administration forms are produced in a known manner by conventional methods.

Norverapamil can also be administered to patients who have already undergone, or are undergoing, other tumor therapies, for example chemotherapy, endocrine therapy, immunotherapy, radiation treatment or surgery, and who have developed resistance, resulting in a decline in the effect of known antitumor agents, which cannot be administered in higher doses owing to side effects.

Norverapamil can also be used for reinforcing the action of antitumor agents (cancerostatics).

The present invention therefore also relates to products containing norverapamil and a cancerostatic as a combination preparation for simultaneous, separate or sequential use in cytostatic therapy.

Particularly suitable cancerostatics are:
(a) antibiotics, such as actinomycin D, doxorubicin (adriamycin), daunorubicin, mithramycin and bleomycin, and other intercalating substances, such as amonafides and mitonafides,
(b) alkaloids, such as vincristine, vinblastine, vindesine, etoposide and teniposide,
(c) alkylating substances, such as cyclophosphamide, nitrosoureas and cisplatin, and
(d) antimetabolites, such as methotrexate, 5-fluorouracil and its analogs, 6-mercaptopurine, 6-thioguanine and cytarabine.

The abovementioned substances can, if desired, be in the form of their salts with physiologically tolerated acids or bases. Preferred physiologically tolerated acids are those stated above.

Particularly suitable physiologically tolerated bases are ammonia, alkali metal hydroxides, in particular those of sodium, of potassium and of lithium, alkaline earth metal hydroxides, in particular those of calcium and of magnesium, and organic bases, such as lower alkylamines, eg. methylamine or ethylamine, cyclohexylamine, substituted lower alkylamines, eg. diethanolamine, triethanolamine or tris-(hydroxymethyl)-aminomethane, piperidine or morpholine.

Norverapamil can be administered together with or separately from the cancerostatics. However, separate, prior administration is preferred. As a rule, norverapamil is administered orally, while the cancerostatics are given orally or parenterally (for example i.v. or i.p.).

The ratio of norverapamil to the cancerostatic depends on the type of cancer to be treated, the stage of the disorder in the patient and the cancerostatic used. As a rule, the ratio is about 1:1 to 500:1. The norverapamil is generally used in an amount of from 200 to 1,000 mg per patient per day for oral administration, from 200 to 300 mg per patient per day for intravenous administration and from 200 to 500 mg per patient per day for intraperitoneal administration. The cancerostatics are administered in the amount also intended for the administration of these substances alone, and which is given in, for example, the Rote Liste 1986 or the scientific prospectuses mentioned therein.

The substances can be in the form of tablets, capsules or coated tablets for oral administration or in the form of injection solutions for parenteral (i.v., i.p. or i.m.) administration. Solutions can also be infused. The administration forms are prepared in a known manner by conventional methods.

EXAMPLES

1. Oblong tablets of the following composition are prepared in a conventional manner:
   500 mg of norverapamil,
   120 mg of lactose,
   60 mg of cellulose,
   3 mg of magnesium stearate,
   50 mg of corn starch and
   15 mg of polyvinylpyrrolidone.

2. 3.0 mg of vincristine sulfate and 500 mg of norverapamil are dissolved in 250 ml of physiological saline solution, sterilized, and introduced into an infusion bottle under sterile conditions.

3. 10 ampoules each containing 1.5 mg of mithramycin from Pfizer (cf. Rote Liste 1985, No. 85,038) and a blister pack of 10 oblong tablets containing norverapamil hydrochloride were packed together in a box. The oblong tablets had been produced in a conventional manner and each tablet contained 500 mg of norverapamil, 120 mg of lactose, 60 mg of cellulose, 3 mg of magnesium stearate, 50 mg of corn starch and 15 mg of polyvinylpyrrolidone.

I claim:

1. A method for treating tumors sensitive to treatment with an antitumor agent in a patient undergoing treatment with such antitumor agent, comprising administering to said patient an effective antitumor amount of norverapamil.

2. A method to claim 1 wherein said effective antitumor amount of norverapamil is within the range of 1:1 to 500:1 of norverapamil to said antitumor agent.

3. A method according to claim 1 wherein said antitumor agent is vincristine sulfate.

4. A method according to claim 1 wherein said antitumor agent is mithramycin.

* * * * *